(12) United States Patent
Steinle et al.

(10) Patent No.: US 7,970,190 B2
(45) Date of Patent: Jun. 28, 2011

(54) METHOD AND DEVICE FOR DETERMINING THE LOCATION OF PELVIC PLANES

(75) Inventors: Wolfgang Steinle, Münich (DE); Rainer Lachner, Münich (DE); Stefan Vilsmeier, Münich (DE)

(73) Assignee: Brainlab AG, Feldkirchen (DE)

( * ) Notice: Subject to any disclaimer, the term of this patent is extended or adjusted under 35 U.S.C. 154(b) by 970 days.

(21) Appl. No.: 11/848,279

(22) Filed: Aug. 31, 2007

(65) Prior Publication Data

US 2008/0056433 A1 Mar. 6, 2008

Related U.S. Application Data

(60) Provisional application No. 60/825,173, filed on Sep. 11, 2006.

(30) Foreign Application Priority Data

Sep. 1, 2006 (EP) ...................................... 06018341

(51) Int. Cl.
*G06K 9/00* (2006.01)

(52) U.S. Cl. .............................. 382/128; 128/922; 378/4

(58) Field of Classification Search .................. 382/100, 382/128, 129, 130, 131, 132; 128/922; 378/4–27
See application file for complete search history.

(56) References Cited

U.S. PATENT DOCUMENTS

| 6,674,883 | B1 * | 1/2004 | Wei et al. ....................... 382/132 |
| 7,496,217 | B2 * | 2/2009 | Tank .............................. 382/128 |
| 7,806,838 | B2 * | 10/2010 | Tsai et al. ..................... 600/587 |
| 2003/0153829 | A1 | 8/2003 | Sarin et al. |
| 2004/0102792 | A1 | 5/2004 | Sarin et al. |
| 2005/0123197 | A1 * | 6/2005 | Tank .............................. 382/173 |
| 2008/0232661 | A1 * | 9/2008 | Habets et al. ................. 382/128 |

FOREIGN PATENT DOCUMENTS

| EP | 1 570 800 | 9/2005 |
| EP | 1 611 863 | 1/2006 |
| WO | 02/062248 | 8/2002 |
| WO | WO 02062248 A1 * | 8/2002 |
| WO | 2004/089192 | 10/2004 |
| WO | 2005/000140 | 1/2005 |

* cited by examiner

*Primary Examiner* — Anand Bhatnagar

(74) *Attorney, Agent, or Firm* — Renner, Otto, Boisselle & Sklar, LLP

(57) ABSTRACT

A method for determining a location of a frontal pelvic plane of a pelvic bone includes ascertaining a position of a pubic point of the pelvic bone; generating at least one x-ray recording of the pelvic bone; ascertaining a straight line in the at least one x-ray recording that passes through the pubic point and a contour of the pelvic bone; and ascertaining the location of the frontal pelvic plane from a rear-projection of the straight line.

14 Claims, 3 Drawing Sheets

METHOD AND DEVICE FOR DETERMINING THE LOCATION OF PELVIC PLANES

RELATED APPLICATION DATA

This application claims priority of U.S. Provisional Application No. 60/825,173 filed on Sep. 11, 2006, which is incorporated herein by reference in its entirety.

FIELD OF THE INVENTION

The present invention relates to medical procedures involving the hip and pelvis and, more particularly, to a method and device for determining a location of the hip or pelvic planes.

BACKGROUND OF THE INVENTION

A location of planes that characterize a position or orientation of the pelvis, in particular the mid-sagittal plane and the frontal pelvic plane, typically are determined prior to hip surgery. The mid-sagittal plane is a vertical plane through the midline of the body that divides the body into right and left halves, while the frontal pelvic plane lies on four points of the pelvis, namely the two pubic points and two spinal points.

If, for example, a new joint cavity is to be inserted into the hip, exact positioning of the new cavity depends on, among other things, the location of the mid-sagittal plane and the location of the frontal pelvic plane. More specifically, when inserting an artificial hip joint, the orientation of the acetabular pelvic implant in relation to these two mutually orthogonal planes (i.e., the mid-sagittal plane and the frontal pelvic plane) is measured or determined.

Depending on what image data are available, these planes can be determined in different ways. For example, if navigation is based on a CT scan, these planes can be defined in the CT volume. Since the CT data set is registered in relation to the patient, these data can be transferred or converted from CT coordinates into patient coordinates. If navigation is performed without imaging methods, these planes can be directly defined on the patient using a pointer, for example.

A method and device for determining a plane of symmetry of a three-dimensional object and, in particular, for determining the mid-sagittal plane of a hip based on two x-ray or fluoroscopic recordings is known from EP 1 570 800 A1, the contents of which is hereby incorporated by reference in its entirety.

Methods for determining the position of a pelvic bone are known from US 2004/0102792 A1 and WO 2004/089192 A2, wherein positions of points on a patient are ascertained by means of a pointer.

SUMMARY OF THE INVENTION

The present invention relates to a method and device for determining a location of hip or pelvic planes. More particularly, the invention relates to determining the location of the frontal pelvic plane from fluoroscopic recordings, which also are referred to as fluoroscopic shots. Once determined, the mid-sagittal plane and the frontal pelvic plane can be used to determine the spatial location or position of a hip, wherein the so-called pubic point lies on both planes.

A method for determining the location of characteristic pelvic planes and in particular for determining the spatial location of the frontal pelvic plane and/or its location relative to the pelvic bone and/or relative to the hip is provided herein. The method may be implemented in conjunction with known methods for determining a location of the mid-sagittal plane (e.g., using the method described in EP 1 570 800 A1 or other known methods such as via pointers). The position of the pubic point (i.e., the point on the pubic bone which protrudes the furthest and/or has the furthest protruding anterior position) is also determined. This point, for example, can be determined from x-ray or fluoroscopic recordings by determining or identifying the position of the characteristically protruding region forming the pubic point, or by palpating by means of a pointer.

It is noted that where the position or location of a point, straight line or plane is mentioned herein, this may be understood to mean either the spatial position or location of a point, straight line or plane or the position or location of a point, straight line or plane relative to the hip or relative to the pelvic bone. It is also assumed that all x-ray or fluoroscopic recordings are "calibrated" (i.e., the direction from which and/or angle at which the respective mapping has been generated is known relative to the mapped object) such that for example a line shown in the respective image is a structure lying in the (rear-)projection plane of the respective mapping device.

Based on at least one calibrated x-ray or fluoroscopic recording, the position or location of the frontal pelvic plane is determined as described herein, wherein the fact that the frontal pelvic plane lies perpendicular on the previously determined mid-sagittal plane and passes through the pubic point and through the crest of the ilium (crista iliaca) can be utilized.

If it is possible to record a lateral fluoroscopic image in which the center-point of projection lies near to or even on the frontal pelvic plane, the location of the frontal pelvic plane can be easily determined from this single recording or image. This determination may be accomplished by rotating a straight line in the fluoroscopic image about the projection of the pubic point such that it contacts the outline or contour of the pelvis, in particular the outline or contour of the crest of the ilium or crista iliaca, as shown in FIG. 1. The frontal pelvic plane is then simply the rear-projection plane of this line, starting from the rotated end position, at which said line passes through the pubic point and the crest of the ilium.

In practice, a small deviation often arises when recording the fluoroscopic image, such that the mid-sagittal plane and the rear-projection plane are not exactly perpendicular to each other. In this case, the rear-projection line can be corrected by rotating it about said line in such a way that it is perpendicular on the mid-sagittal plane. This rotation can be performed either automatically or by a user; for this purpose, a graphic user interface, for example, can be provided.

If a lateral fluoroscopic image cannot be recorded, for example because the patient is positioned such that he/she would have to be rotated for this purpose (which is not preferred), or exhibits too much fatty tissue that is unfavorably arranged for the recording, the location of the frontal pelvic plane can be determined by taking two x-ray or fluoroscopic recordings from different recording or viewing directions. In each of the recordings, a line again can be respectively placed through the pubic point and rotated until said line abuts a contour or outline of the crest of the ilium. By rear-projecting these two lines abutting two points of the crest of the ilium, two planes can be obtained that intersect in a line or straight line lying on the frontal pelvic plane. If the intersection line ascertained in this way is mirrored in the mid-sagittal plane, another line on the frontal pelvic plane can be obtained, wherein the frontal pelvic plane can be determined by these two lines.

If a lateral fluoroscopic image cannot be generated, then the same two x-ray or fluoroscopic recordings used to determine the location of the frontal pelvic plane can be used to determine the location of the mid-sagittal plane, for example, in accordance with the teaching of EP 1 570 800 A1. However, it is also possible to only use one image or to use other fluoroscopic images. These images may be used in combination with images or recordings that are already available.

The patient and preferably the pelvic bone can be connected to at least one marker or marker system, such as a reference star, for example, to enable localization or tracking of the pelvic bone in combination with a known tracking system. It is equally possible for the patient and the pelvic bone to be held in a stationary or fixed position, for example, by means of a known frame, wherein at least one marker or a marker array can be connected to the frame or on a device connected to the frame, such as an operating table, for example.

By using the method described herein, it is possible to easily determine all the data necessary for positioning an artificial hip joint and, in particular, the spatial position or location of the pelvic bone or its characteristic planes, without having to manually detect a point on the hip, for example by means of a pointer. The method can be performed, for example, based on only two fluoroscopic recordings. The method is in particular advantageous because an ASIS (anterior superior iliac spine) point, which is not easy to identify, does not have to be identified in order to ascertain the location of the frontal pelvic plane.

At least two two-dimensional mappings of the pelvic bone can be generated from recordings (e.g., via x-rays or so-called fluoroscopic shots), wherein the recordings may be obtained from different angles. Preferably, the recordings of the pelvis are obtained from two different directions, wherein the centers of projection enclose an angle of 5 degrees to 30 degrees, e.g., an angle of 10 degrees, with the object. It is also possible to take a number of recordings of the object from different directions, wherein the method described herein can be performed, for example, using two two-dimensional mappings of the three-dimensional object in each case. This can increase the accuracy in ascertaining the mid-sagittal plane and the frontal pelvic plane of the pelvis. A reference star or marker can be directly attached to the pelvic bone to be mapped so as to ascertain the spatial relationship of the object relative to the centers of projection and associated mapping planes, wherein these localization data can be used to perform the method described herein.

Also provided is a computer program which, when it is loaded onto a computer or is running on a computer, performs one or more of the method steps described above, and to a program storage medium or computer program product comprising such a program.

A device for determining the location of the frontal pelvic plane can include, for example, a C-arm having at least one center of projection, such as for example a radiation source, and at least one projection plane. Using the C-arm and the at least one projection plane, a two-dimensional mapping of the three-dimensional object can be generated. By rotating the center of projection and the projection plane about the pelvis, or by using another center of projection or another projection plane, it is possible to generate at least one other two-dimensional mapping of the three-dimensional object that is advantageous for performing the method described herein. At least one marker or reference star can be directly or indirectly attached to the object, thus enabling the positional relationship of the object relative to the at least one center of projection and/or the at least one projection plane to be ascertained. A computational unit also can be provided that receives one and preferably at least two two-dimensional mapping data of the three-dimensional object, the spatial location data of the object, the center of projection, and the mapping plane. Using this data, the computational unit can perform the method as described herein.

BRIEF DESCRIPTION OF THE DRAWINGS

The forgoing and other features of the invention are hereinafter discussed with reference to the drawing.

DETAILED DESCRIPTION

Figure 1:
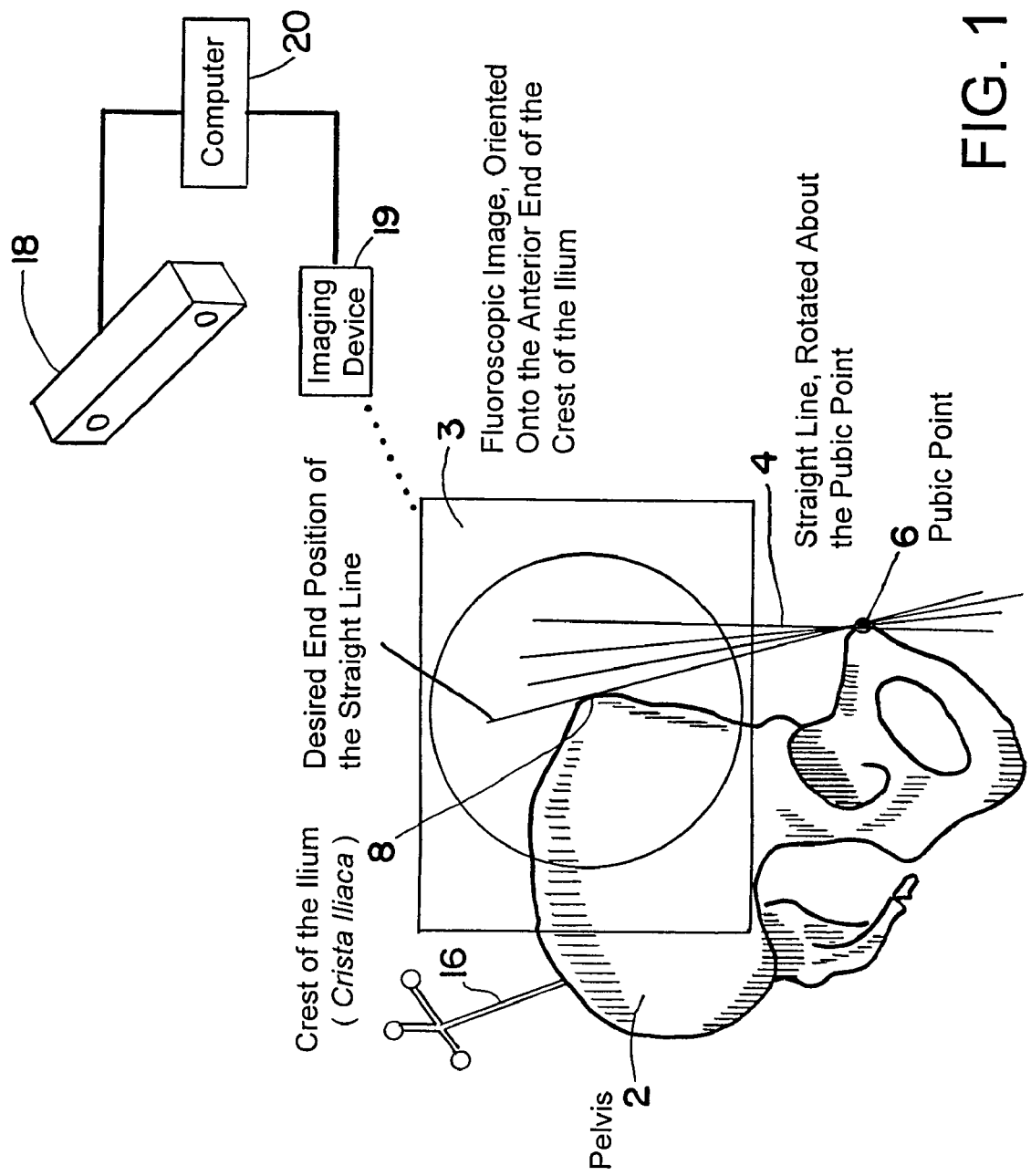
FIG. 1 illustrates an exemplary method for determining the frontal pelvic plane by means of a lateral fluoroscopic image in accordance with the invention.

FIG. 1 shows a marker or marker array 16 attached to a pelvic bone 2 and monitored by a tracking system 18 (e.g., a camera-based tracking system or the like). Based on data obtained from the marker array 16, a location of the pelvic bone 2 in three-dimensional space can be ascertained. The positional data can be provided to a computer 20, which may be a standalone computer or a computer of a medical navigation system, for example.

Further, FIG. 1 shows a lateral recording 3 of the pelvic bone 2, which can be obtained from an imaging device 19, such as a C-arm apparatus, for example. The imaging device 19 can be communicatively coupled to the computer 20 so as to provide the recording thereto.

In the lateral recording 3, a straight line 4 is placed through the pubic point 6 of the pelvic bone 2 and rotated about this point until it abuts the crest of the ilium (crista iliaca) 8 in its end position. Because the mid-sagittal plane is the image plane in the lateral recording, and the rear-projection of the straight line 4 generates a plane that is perpendicular on the mid-sagittal plane and passes through both the pubic point 6 and the crest of the ilium 8, the plane found by this rear-projection is also the frontal pelvic plane, such that its spatial location or location relative to the pelvic bone 2 is determined. The method for determining the location of the frontal pelvic plane may be implemented by the computer 20, wherein the determined location can be provided on an output device, such as a display or the like.

Figure 2:
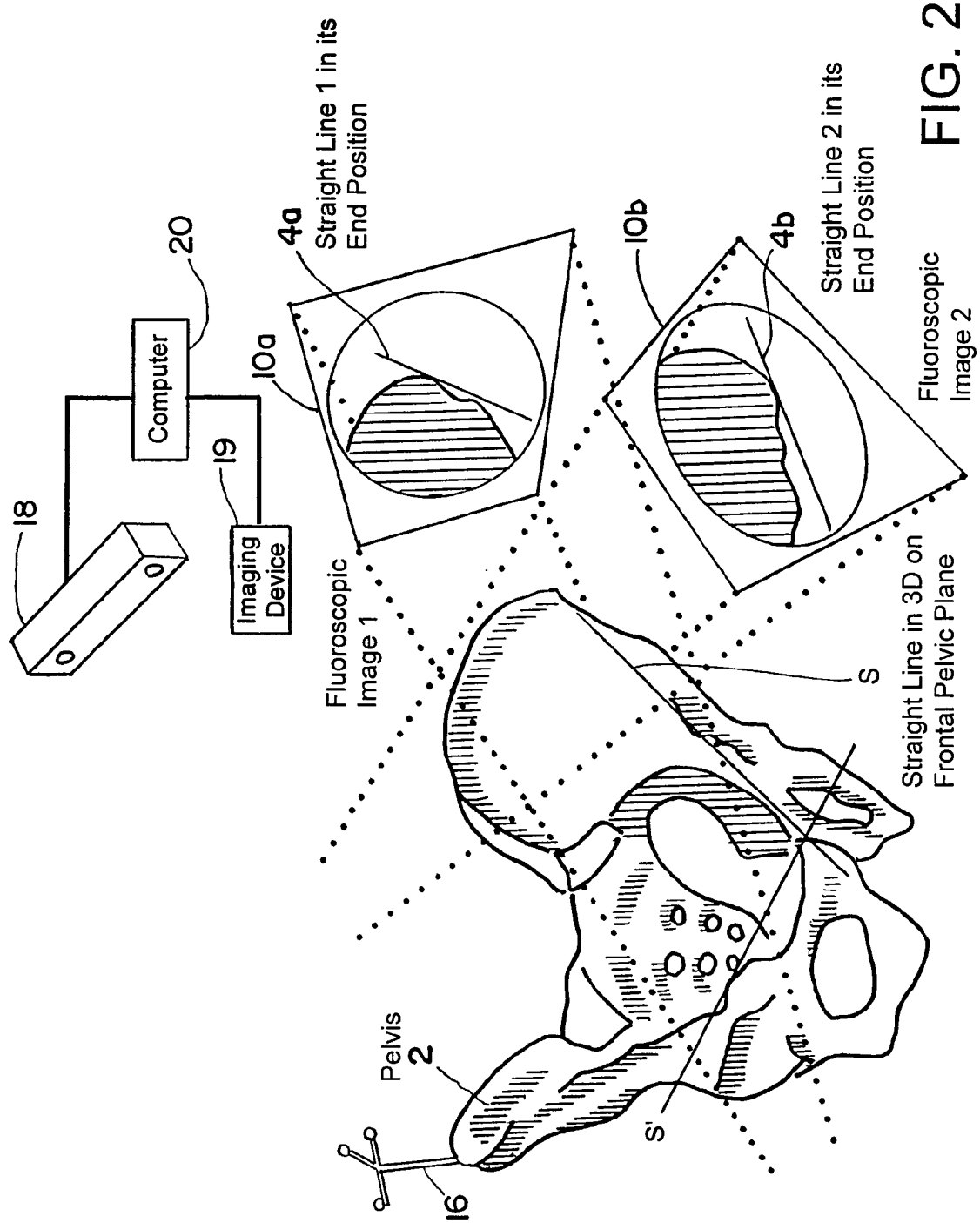
FIG. 2 illustrates another exemplary method for determining the location of the frontal pelvic plane by means of two fluoroscopic images recorded from different directions in accordance with the invention.

FIG. 2 illustrates another method for determining the location of the frontal pelvic plane. In FIG. 2, there is shown a marker or marker array 16 attached to the pelvic bone 2 and monitored by a tracking system 18 to obtain a location of the pelvic bone in three-dimensional space. This positional data can be provided to computer 20 as noted above. Further, an imaging device, such as a C-arm imaging device 19, is communicatively coupled to the computer and provides imaging data thereto.

Unlike the method shown in FIG. 1, the method of FIG. 2 does not utilize a lateral recording of the pelvic bone 2. Instead, two recordings 10a and 10b of the pelvic bone 2 from suitable, different directions are generated. As described in FIG. 1, straight lines 4a and 4b are placed through the pubic point 6 for the respective fluoroscopic images, and the lines 4a and 4b are rotated until they abut a contour of the pelvic bone 2 in the respective fluoroscopic image 10a and 10b. By rear-projecting the respective straight lines 4a and 4b, two planes are obtained that meet in the straight intersection line indicated as S. This straight intersection line S is mirrored in the previously ascertained mid-sagittal plane, such that the mirrored straight line S' is obtained. The plane defined by the two straight lines S and S' is the frontal pelvic plane, the spatial location of which or location relative to the pelvic bone 2 has been determined from two recordings (e.g., two fluoroscopic recordings or x-ray recordings) obtained from different directions.

Figure 3:
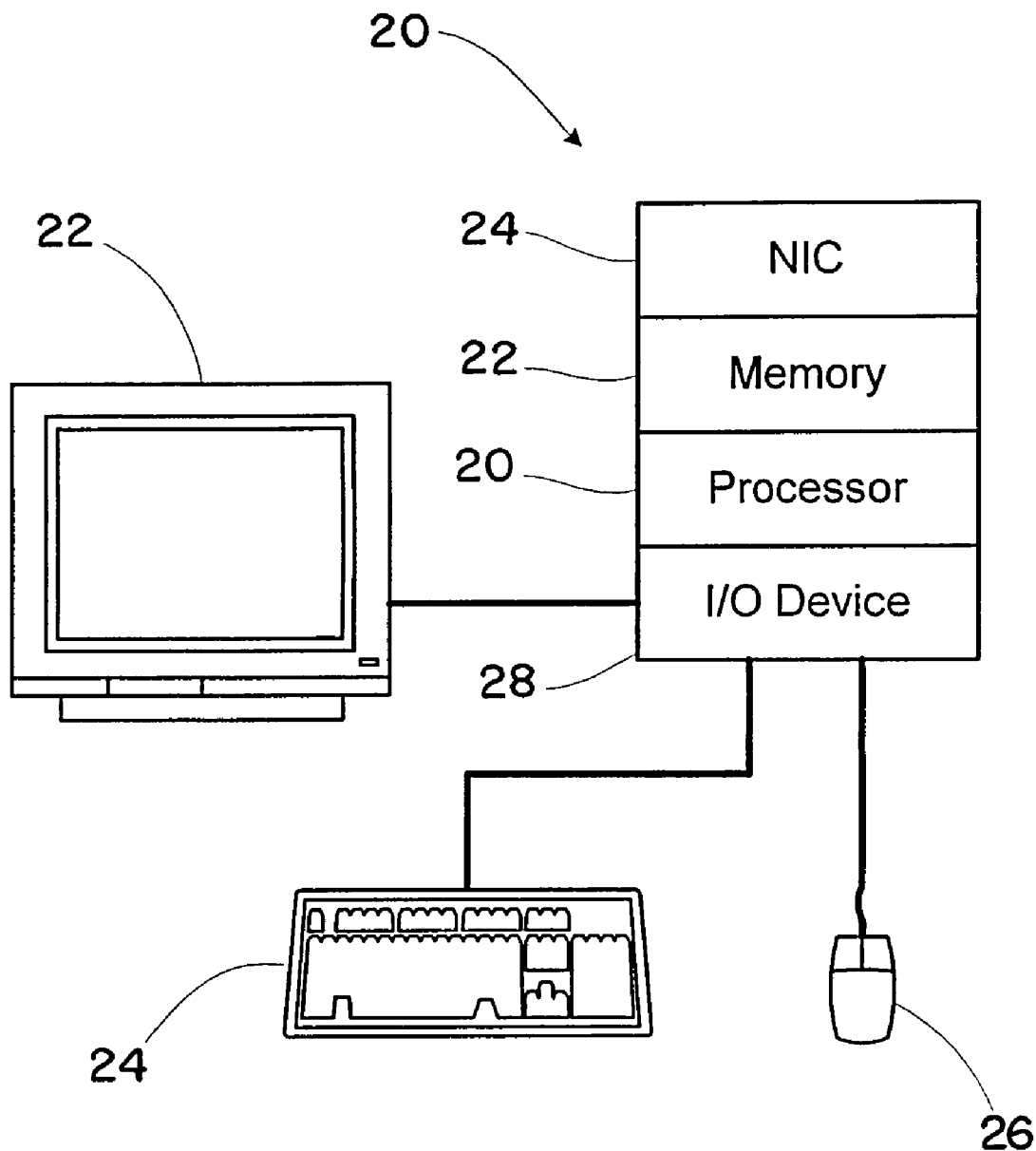
FIG. 3 is a block diagram of an exemplary computer system that can be used to implement the method described herein.

Moving now to FIG. 3 there is shown a block diagram of an exemplary computer 20 that may be used to implement one or more of the methods described herein. The computer 20 may include a display 22 for viewing system information, and a keyboard 24 and pointing device 26 for data entry, screen navigation, etc. A computer mouse or other device that points to or otherwise identifies a location, action, etc., e.g., by a point and click method or some other method, are examples of a pointing device 26. Alternatively, a touch screen (not shown) may be used in place of the keyboard 24 and pointing device 26. The display 22, keyboard 24 and mouse 26 communicate with a processor via an input/output device 28, such as a video card and/or serial port (e.g., a USB port or the like).

A processor 30, such as an AMD Athlon 64® processor or an Intel Pentium IV® processor, combined with a memory 32 execute programs to perform various functions, such as data entry, numerical calculations, screen display, system setup, etc. The memory 32 may comprise several devices, including volatile and non-volatile memory components. Accordingly, the memory 32 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 30 and the memory 32 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 34 allows the computer 20 to communicate with other devices.

A person having ordinary skill in the art of computer programming and applications of programming for computer systems would be able in view of the description provided herein to program a computer system 20 to operate and to carry out the functions described herein. Accordingly, details as to the specific programming code have been omitted for the sake of brevity. Also, while software in the memory 32 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining a location of a frontal pelvic plane of a pelvic bone, comprising:
   ascertaining a position of a pubic point of the pelvic bone;
   generating at least one x-ray recording of the pelvic bone;
   ascertaining a straight line in the at least one x-ray recording that passes through the pubic point and a contour of the pelvic bone;
   ascertaining the location of the frontal pelvic plane from a rear-projection of the straight line; and
   outputting the ascertained location of the frontal pelvic plane.

2. The method according to claim 1, wherein generating at least one x-ray recording includes generating a lateral x-ray recording of the pelvic bone, and wherein a plane ascertained by rear-projecting the straight line is the frontal pelvic plane.

3. The method according to claim 1, wherein ascertaining the straight line through the contour of the pelvic bone includes a contour of the crest of the ilium or crista iliaca.

4. The method according to claim 1, further comprising determining a location of a mid-sagittal plane, and wherein
   generating at least one x-ray recording includes generating at least first and second x-ray recordings of the pelvic bone from different directions;
   ascertaining a straight line includes ascertaining a straight line in each of the first and second x-ray recordings, wherein each straight line passes through the pubic point and abuts a contour of the pelvic bone; and
   ascertaining the location of the frontal pelvic plane from the rear-projection includes generating at least two planes by rear-projecting the respective straight lines to form a first straight intersection line, and mirroring the straight intersection line about the mid-sagittal plane to obtain a second straight intersection line, wherein the frontal pelvic plane is defined by the first and second straight intersection lines.

5. The method according to claim 4, wherein generating first and second x-ray recordings from different directions includes using centers of projection that enclose an angle of 5 degrees to 30 degrees.

6. The method according to claim 1, further comprising:
directly or indirectly attaching at least one trackable marker to the pelvic bone; and
ascertaining a spatial location of the pelvic bone from the at least one marker via a medical navigation system.

7. The method according to claim 1, further comprising using a holding device to fix the pelvic bone in a stationary position, wherein at least one trackable marker is coupled to the frame or to a structure connected to the frame.

8. The method according to claim 1, further comprising:
wherein generating at least one x-ray recording of the pelvic bone includes generating a plurality of fluoroscopic images of the pelvic bone; and
ascertaining the frontal pelvic plane from two fluoroscopic images of the plurality of fluoroscopic images.

9. A computer program embodied on a non-transitory computer readable medium for determining a location of a frontal pelvic plane of a pelvic bone, comprising:
code that ascertains a position of a pubic point of the pelvic bone;
code that directs the generation of at least one x-ray recording of the pelvic bone;
code that ascertains a straight line in the at least one x-ray recording that passes through the pubic point and a contour of the pelvic bone; and
code that ascertains the location of the frontal pelvic plane from a rear-projection of the straight line.

10. A device for determining a location of a frontal pelvic plane of a pelvic bone from at least one two-dimensional recording of the pelvic bone, comprising:

a processor and memory;
logic stored in the memory and executable by the processor, said logic including
logic that ascertains a position of a pubic point of the pelvic bone;
logic that directs the generation of at least one x-ray recording of the pelvic bone;
logic that ascertains a straight line in the at least one x-ray recording that passes through the pubic point and a contour of the pelvic bone; and
logic that ascertains the location of the frontal pelvic plane from a rear-projection of the straight line.

11. A system for determining a location of a frontal pelvic plane of a pelvic bone from at least one two-dimensional recording of the pelvic bone, comprising:
at least one trackable marker connectable to the pelvic bone; and
a computational unit configured to
a) receive at least one x-ray recording of the pelvic bone;
b) receive position data corresponding to the pelvic bone, said position data based on data obtained from the at least one trackable marker;
c) ascertain a position of a pubic point of the pelvic bone based on the position data;
d) ascertain a straight line in the at least one x-ray recording that passes through the pubic point and a contour of the pelvic bone; and
e) ascertain the location of the frontal pelvic plane from a rear-projection of the straight line.

12. The system according to claim 11, further comprising an imaging device configured to obtain the at least one x-ray recording.

13. The system according to claim 12, wherein the imaging device comprises an x-ray radiation source.

14. The system according to claim 11, further comprising a tracking system configured to determine a spatial position of the pelvic bone based on data corresponding to the at least one trackable marker.

* * * * *